(12) United States Patent
Biedermann et al.

(10) Patent No.: US 10,682,169 B2
(45) Date of Patent: Jun. 16, 2020

(54) BONE SCREW

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Helmar Rapp, Deißlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 272 days.

(21) Appl. No.: 15/687,345

(22) Filed: Aug. 25, 2017

(65) Prior Publication Data

US 2018/0070999 A1     Mar. 15, 2018

Related U.S. Application Data

(63) Continuation of application No. 12/985,183, filed on Jan. 5, 2011, now Pat. No. 9,770,277.
(Continued)

(30) Foreign Application Priority Data

Jan. 8, 2010  (EP) .................................... 10150373

(51) Int. Cl.
  *A61B 17/86*     (2006.01)
(52) U.S. Cl.
  CPC ........ *A61B 17/8685* (2013.01); *A61B 17/864* (2013.01); *A61B 17/8605* (2013.01); *A61B 17/8635* (2013.01)
(58) Field of Classification Search
  CPC .............. A61B 17/8605; A61B 17/864; A61B 17/8685
  See application file for complete search history.

(56) References Cited

U.S. PATENT DOCUMENTS 3,182,658 A * 5/1965 Klinger ................ A62B 18/082
                                                         128/201.12
4,484,570 A * 11/1984 Sutter ................ A61B 17/8038
                                                         606/282
(Continued)

FOREIGN PATENT DOCUMENTS

EP      1 430 846 A1   6/2004
EP      1 749 490 A1   2/2007
(Continued)

OTHER PUBLICATIONS

Extended European Search Report dated Mar. 3, 2010 for priority application No. EP 10 15 0373.8, 7 sheets.
(Continued)

*Primary Examiner* — Zade Coley
(74) *Attorney, Agent, or Firm* — Lewis Roca Rothgerber Christie LLP (57)  ABSTRACT

A bone screw is provided including a tubular body and a head as separate parts. The tubular body has a first end, a second end, a tubular wall defining a cavity and a plurality of openings extending through the tubular wall into the cavity. The tubular body also includes a continuous exterior bone thread on an exterior tubular surface of the tubular wall. The continuous exterior bone thread extends for at least one full revolution about the tubular surface. The head defines an inner bore and includes an engagement structure to engage with a driver to advance the bone screw in the bone when a rotating force from the driver is applied to the engagement structure in a first direction, and a connection structure to connect to the tubular body at the first end. The head is connected to the tubular body by the connection structure in such a way that the head is locked against disconnection from the tubular body when a rotating force
(Continued)

from a driver is applied to the engagement structure in a second direction opposite to the first direction.

20 Claims, 7 Drawing Sheets

Related U.S. Application Data (60) Provisional application No. 61/293,433, filed on Jan. 8, 2010.

(56) References Cited

U.S. PATENT DOCUMENTS

| | | | | |
|---|---|---|---|---|
| 4,858,601 | A * | 8/1989 | Glisson | A61B 17/8685 606/916 |
| 5,584,629 | A * | 12/1996 | Bailey | A61C 8/0022 403/334 |
| 5,827,285 | A * | 10/1998 | Bramlet | A61B 17/68 606/60 |
| 5,964,767 | A * | 10/1999 | Tapia | A61B 17/3421 411/177 |
| 6,017,177 | A * | 1/2000 | Lanham | F16B 23/003 411/402 |
| 6,034,295 | A * | 3/2000 | Rehberg | A61B 17/72 433/201.1 |
| 6,077,262 | A * | 6/2000 | Schlapfer | A61B 17/7032 606/264 |
| 6,079,923 | A * | 6/2000 | Ross | F16B 4/004 411/107 |
| 6,517,542 | B1 * | 2/2003 | Papay | A61B 17/0401 606/232 |
| 6,736,579 | B2 * | 5/2004 | Lonnqvist | B25B 13/485 411/396 |
| 7,409,070 | B2 * | 8/2008 | Pitulia | A61F 2/18 381/324 |
| 8,048,132 | B2 * | 11/2011 | Wu | A61B 17/7032 606/264 |
| 8,137,389 | B2 * | 3/2012 | Biedermann | A61B 17/864 606/301 |
| 8,968,372 | B2 * | 3/2015 | Biedermann | A61B 17/864 606/304 |
| 2001/0001119 | A1 * | 5/2001 | Lombardo | A61B 17/7037 606/264 |
| 2002/0042615 | A1 * | 4/2002 | Graf | A61F 2/0811 606/312 |
| 2002/0082598 | A1 | 6/2002 | Teitelbaum | |
| 2002/0169507 | A1 | 11/2002 | Malone | |
| 2004/0015172 | A1 * | 1/2004 | Biedermann | A61B 17/864 606/304 |
| 2004/0097953 | A1 * | 5/2004 | Krenkel | A61B 17/666 606/105 |
| 2004/0122431 | A1 * | 6/2004 | Biedermann | A61B 17/864 606/62 |
| 2004/0147929 | A1 * | 7/2004 | Biedermann | A61B 17/7001 606/266 |
| 2005/0059972 | A1 | 3/2005 | Biscup | |
| 2005/0192571 | A1 | 9/2005 | Abdelgany | |
| 2006/0095038 | A1 * | 5/2006 | Jackson | A61B 17/7032 606/306 |
| 2007/0009853 | A1 * | 1/2007 | Pitulia | A61F 2/18 433/173 |
| 2007/0093832 | A1 * | 4/2007 | Abdelgany | A61B 17/7037 606/250 |
| 2007/0270848 | A1 * | 11/2007 | Lin | A61B 17/746 606/65 |
| 2007/0274800 | A1 * | 11/2007 | Mikkonen | A61B 17/862 411/15 |
| 2008/0132959 | A1 * | 6/2008 | Mikkonen | A61B 17/862 606/308 |
| 2008/0312692 | A1 * | 12/2008 | Brennan | A61B 17/7005 606/246 |
| 2009/0082817 | A1 * | 3/2009 | Jinton | A61C 8/0025 606/301 |
| 2009/0192551 | A1 * | 7/2009 | Cianfrani | A61B 17/686 606/301 |
| 2009/0192553 | A1 * | 7/2009 | Maguire | A61B 17/8038 606/305 |
| 2009/0326534 | A1 | 12/2009 | Yamazaki et al. | |
| 2011/0004245 | A1 * | 1/2011 | Wu | A61B 17/7032 606/246 |
| 2011/0106172 | A1 * | 5/2011 | Wallenstein | A61B 17/8685 606/286 |
| 2011/0137352 | A1 * | 6/2011 | Biedermann | A61B 17/8635 606/305 |

FOREIGN PATENT DOCUMENTS

| | | |
|---|---|---|
| EP | 1 825 826 A1 | 8/2007 |
| EP | 1 925 263 A1 | 5/2008 |
| KR | 2003-0028685 A | 4/2003 |
| KR | 2003-0068157 A | 8/2003 |
| KR | 10-2008-0068674 A | 7/2008 |
| WO | WO 02/43601 A2 | 6/2002 |
| WO | WO 2007/041265 A1 | 4/2007 |
| WO | WO 2009/114014 A1 | 9/2009 |

OTHER PUBLICATIONS

Korean Notice of Allowance for Application No. KR 10-2010-0136855, dated Jan. 30, 2015, and English translation (6 pages).

* cited by examiner

BONE SCREW

CROSS-REFERENCE TO RELATED APPLICATIONS

This application is a continuation of U.S. patent application Ser. No. 12/985,183, filed Jan. 5, 2011, which claims priority to and the benefit of U.S. Provisional Application No. 61/293,433, filed Jan. 8, 2010, the entire contents of each of which are incorporated herein by reference. This Application also claims priority to and the benefit of EP 10 150 373.8, filed in the European Patent Office on Jan. 8, 2010, the entire contents of which are incorporated herein by reference.

BACKGROUND

The invention relates to a bone screw. In particular, the invention relates to a bone screw that can be used as an anchor screw and a fusion screw that fuses with the surrounding bone material.

A bone screw that can be used as a fusion screw is known from US 2004/0015172 A1. This bone screw has a tubular thread section with a bone thread and with a plurality of recesses in its wall, a head, and a tip that can be connected to the tubular thread section. In use, the tubular portion can be filled with bone material or other growth promoting material and then the tip and/or the head are connected to the tubular portion. Usually the screw is inserted into a core hole in the bone, which is prepared in advance. After insertion of the screw into the bone, fusion of the screw with the surrounding bone material takes place. The screw can act as a traction element to connect shattered or split-off parts of bones together by means of the screw.

SUMMARY

It is the object of the invention to provide an improved bone screw of the aforementioned type, the position of which in the bone can be corrected after insertion and which can be easily removed later, if required.

The bone screw according to the invention is fillable with a substance to support fusion and is precisely positionable. When the bone screw is inserted into a core hole that has been prepared in advance, the bone thread at an exterior wall surface engages the bone and the screw is advanced by screwing it deeper into the bone by means of a screw driver. To adjust the position of the bone screw, it might be necessary to screw it back out to reposition the screw. This is facilitated, since the head and the tubular body of the bone screw are firmly connected without a risk of loosening or disconnection.

The bone screw can act as a bone anchor or can be used to connect broken elements of bones or as a support beam to strengthen weak bones.

In certain situations, it might be clinically necessary to remove an implanted bone screw at a later stage, when the bone screw may have already fused with the surrounding bone material. Since the head and the tubular body are firmly connected, it is possible to remove a bone screw that has already fused with the surrounding bone material.

Further features and advantages of the invention will become apparent from the description of embodiments of the invention by means of the accompanying drawings.

DETAILED DESCRIPTION

The bone screw according to a first embodiment as shown in FIGS. 1 to 7 comprises a tubular body 1 with an open first end 2 and a second end 3 and a screw axis L. In the example shown, the tubular body is cylindrical. The tubular body has a tubular wall defining a cavity. On the exterior surface of the tubular wall, a so-called bone thread 4 is provided. In the embodiment shown, the bone thread is provided along the whole length of the tubular body. The bone thread 4 is configured to cut into the bone when the bone screw is screwed into the bone. Further, a plurality of openings 5 are located in the tubular wall, which extend entirely through the tubular wall into the cavity. The plurality of openings 5 are shown as diamond-shaped and are located between the crests of the bone thread 4. However, any other variations of the shapes and locations of the plurality of openings 5 are conceivable. The cavity provided by the tubular body 1 has a volume that is suitable for accommodating bone material. The wall thickness of the tubular body is preferably smaller than about 15% of the outer diameter of the tubular body.

Figure 5:
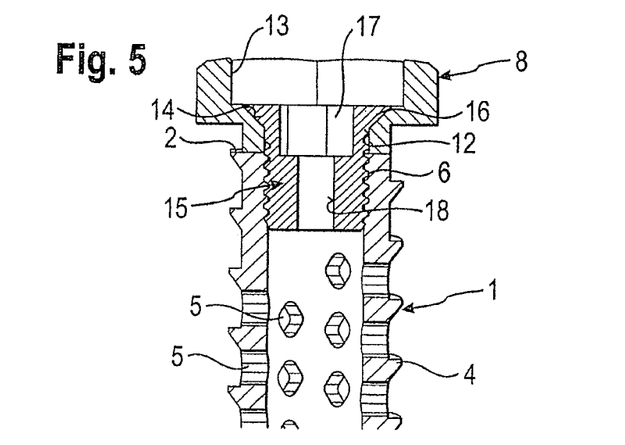
FIG. 5 shows a sectional view of the bone screw of FIG. 3 in an assembled state, the section being taken in a plane containing the screw axis.

As shown in FIG. 5, the tubular body 1 has in the region of its first end 2 an internal thread 6 provided on its interior wall surface. At the first end 2 a plurality of recesses 7 are provided in the wall of the tubular body, which extend in the axial direction from the first end 2 to a certain distance in direction of the second end 3. Seen in the radial direction, the recesses extend completely through the wall of the tubular body. In the embodiment shown, four triangular recesses 7 are provided at equidistant locations in the circumferential direction of the edge of the first end 2.

The bone screw further comprises a head 8 that is connectable to the first end 2. The head 8 is substantially cylindrical and has an outer diameter that is greater than the outer diameter of the tubular body 1. The head 8 has a first end 9 facing away from the tubular body 1 and a second end 10 facing the first end 2 of the tubular body. At its second end 10, the head 8 has a plurality of projections 11, the shape and location of which is such that the projections 11 engage the recesses 7 of the tubular body 1 so that a form-fit connection between the head 8 and the tubular body 1 is provided. In this embodiment, four equidistantly-located triangular projections extend from the second end 10 of the head 8. Instead of recesses at the tubular body and projections at the head, recesses can be present at the head and projections can be present at the tubular body, or the head and the tubular body can have both recesses and projections. The head 8 in this embodiment is cannulated. It comprises a coaxial bore 12 extending from the first end 9 to the second end 10 completely through the head.

At its first end 9 a recess 13 is provided, which is configured to engage with a screw driver used to screw the bone screw into the bone by rotating the driver in a first direction that is the screw-in direction. The recess 13 has an inner diameter that is larger than the inner diameter of the coaxial bore 12. The shape of the recess is, for example, a hexagon shape. However, any other shape that is suitable for engagement with a screw driver can be used. Such other shapes can be, for example, square shape or any other polygon shape or star shape, for example a Torx® shape. Between the recess 13 and the second end 10 of the head 8 there is a transition portion 14 that is, for example, a tapered portion that can act as an abutment for a securing screw with tapered head to be described below. However, the transition portion can have another shape adapted to the shape of the head of the securing screw or can be omitted. The second end 10 of the head 8 of the bone screw has preferably a flat surface in order to provide an abutment for the bone surface.

The bone screw also comprises a securing element 15 in the form of a screw, the screw thread of which cooperates with the internal thread 6 provided at the interior wall surface of the tubular body 1. The screw has a tapered head 16 abutting against the tapered transition portion 14 of the head. Further, a recess 17, for example, a polygon recess, is provided for engagement with a screw driver.

By means of the above described design, the head 8, which has the engagement structure for the screw driver to insert the screw into the bone, is connected by a form-fit connection to the tubular body, which prevents the head from being disconnected from the tubular body in the case that the screw driver is rotated in the reverse direction of the screw-in direction. Further, the connection between the head and the tubular body via the securing element is independent from the force acting onto the head when the screw is being screwed in.

For the securing element, other screw types or other devices such as a bayonet locking device can be used.

Figure 1:
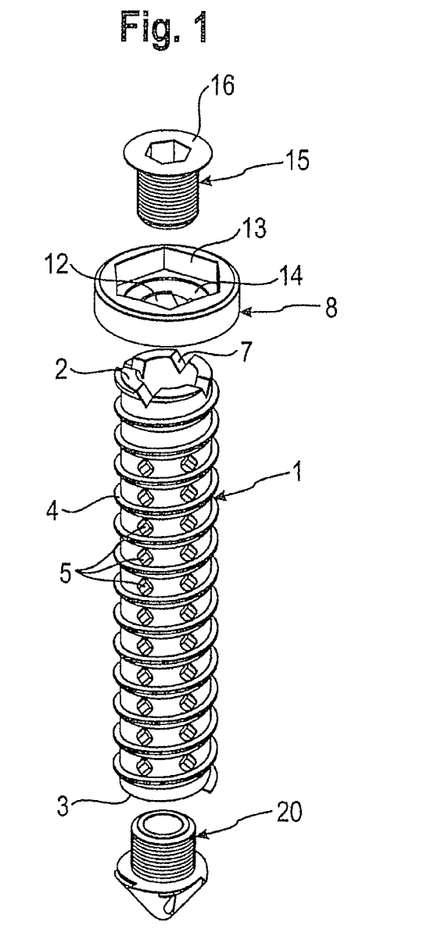
FIG. 1 shows a perspective exploded view of a bone screw according to a first embodiment.
Figure 2:
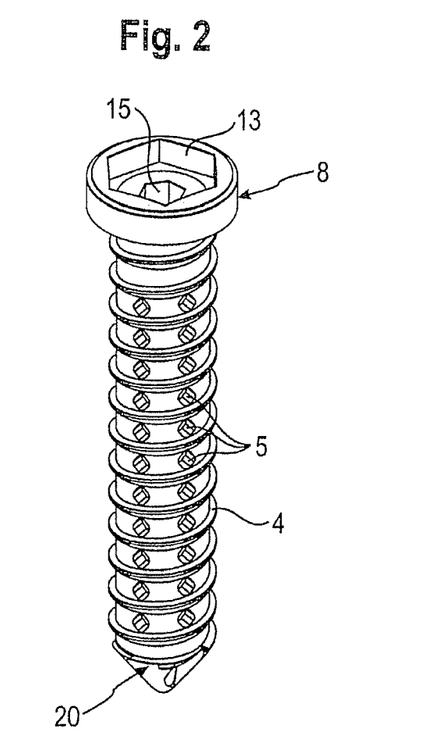
FIG. 2 shows a perspective view of the bone screw of FIG. 1 in an assembled state.
Figure 3:
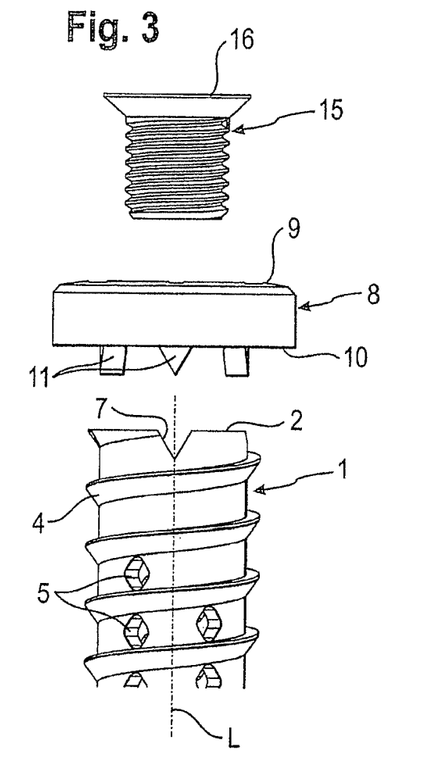
FIG. 3 shows an enlarged exploded side view of a bone screw according to the first embodiment, a tubular portion being shown only in part.
Figure 4:
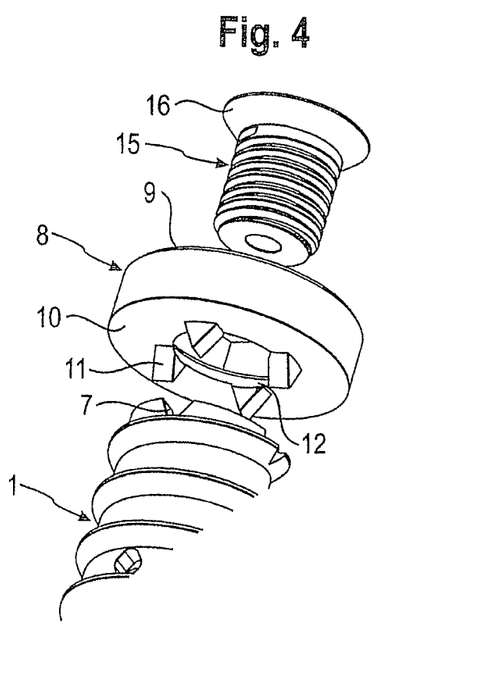
FIG. 4 shows a perspective exploded view of the bone screw of FIG. 3.
Figure 6:
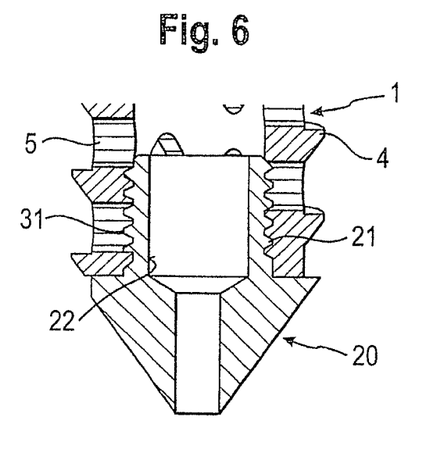
FIG. 6 shows an sectional view of an enlarged portion of the bone screw according to FIG. 1 in the region of the tip, the section being taken in a plane containing the screw axis.
Figure 7:
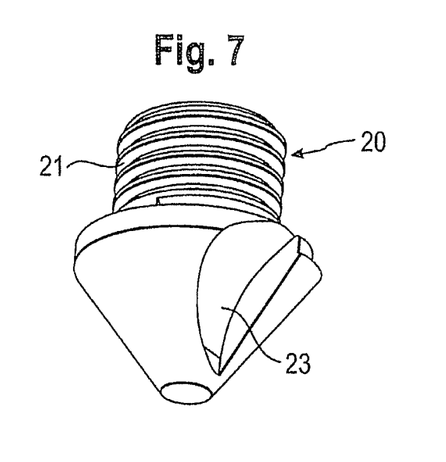
FIG. 7 shows an enlarged perspective view of the tip.

As shown in FIGS. 1, 6 and 7, the bone screw further has a separate tip 20 having a projection. The tip 20 in this embodiment is detachably connected to the tubular body 1. For this purpose, the tubular body 1 has adjacent to its second end 3 an internal thread 31, which can be engaged by an external thread 21 provided at the projection of the tip 20. In this embodiment, the tip 20 is cannulated. It has a coaxial bore 22 extending completely through the tip 20, which narrows towards the tip end opposite the projection. The tip 20 that is shown as an example also has a self-cutting structure 23, which allows the tip 20 to cut the bone when the bone screw is rotated so that it is not necessary to prepare a core hole in advance.

Other kinds of tips are conceivable. For example, the design of the tip can be such that it can be connected via a press-fit connection to the tubular body. Tips without self-cutting structures or without coaxial bores are also conceivable. Finally, it is also possible that the tip is integrally formed with the tubular body 1.

The coaxial bore 12 in the head and the coaxial bore 22 in the tip can serve as a guide structure for guiding a guide wire therethrough. They also can serve as a channel for introducing liquid bone cement or fluid drugs.

All parts of the bone screw are made of a body-compatible material such as a body-compatible metal, for example stainless steel or titanium; a body-compatible metal alloy, for example Nitinol; a body-compatible plastic material, for example PEEK; or combinations thereof.

In addition, the tubular body or the other parts of the bone screw can be coated with an in-growth promoting material or can be roughened to enhance in-growth of bone or vessels.

Figures 8A, 8B:
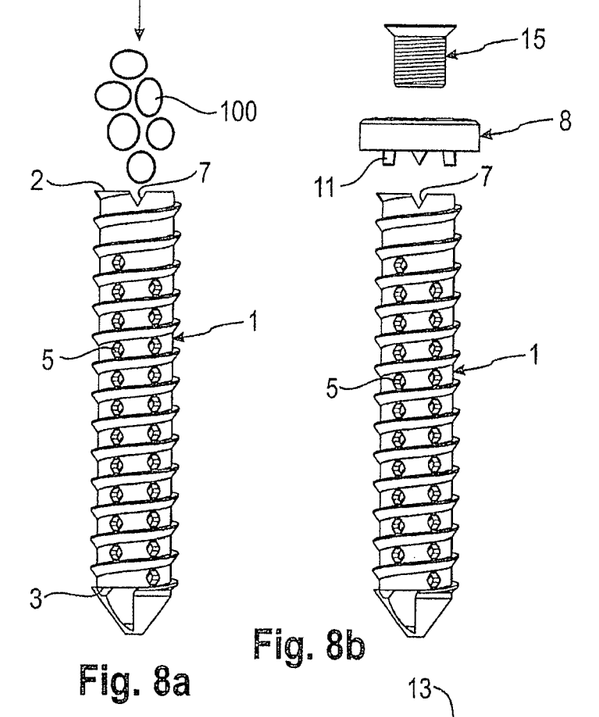
FIGS. 8a to 8d show steps of using the bone screw according to the first embodiment.
Figure 8C:
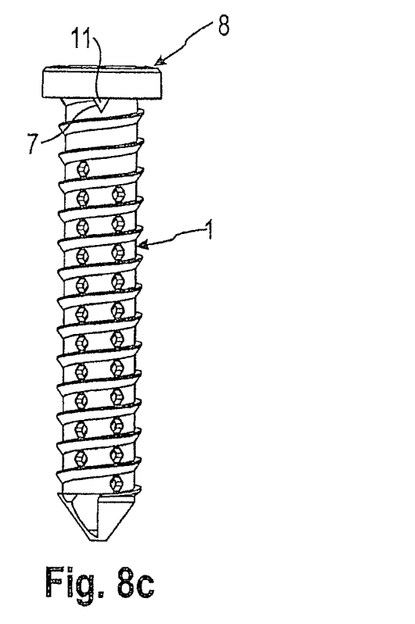
Figure 8D:
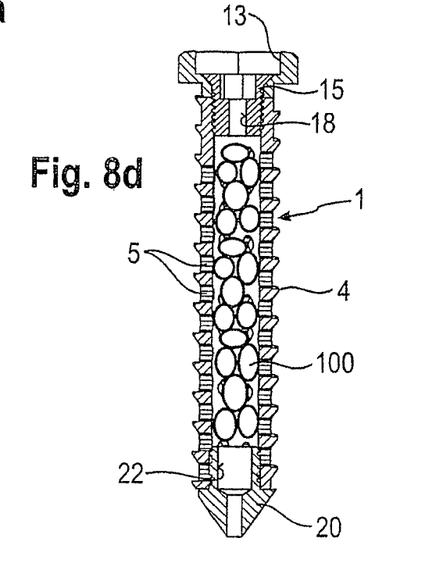

The steps of using the bone screw are shown in FIGS. 8a to 8d. In a first step shown in FIG. 8a, the tip 20 is mounted onto the second end of the tubular body 1. Then, bone chips 100 are filled into the cavity provided by the tubular body 1. Then, as shown in FIG. 8b, the head 8 and the securing screw 15 are mounted onto the first end of the tubular body 1. The head 8 is mounted such that the projections 11 at the second end 10 of the head engage the recesses 7 at the first end 2 of the tubular body. In this position, the securing screw 15 is introduced and tightened, so that the bone screw is closed, as shown in the side view of FIG. 8c and the sectional view of FIG. 8d.

The thus-prepared bone screw can be inserted into a core hole in the bone, which has been prepared in advance. The recess 13 is engaged with the screw driver (not shown) and the bone screw is advanced into the core hole by rotating the screwdriver in the screw-in direction. Slight corrections of the position of the bone screw in the core hole can be made by rotating the screwdriver in a reverse direction, so that the screw is screwed back out. Because of the shape-fit connection between the head and the tubular body, this is easily possible without the risk of loosening or disconnection of the head and the tubular body. After a certain time, fusion of the surrounding bone with the bone screw takes place.

In another embodiment of use, the coaxial bores 18 and 22 of the securing screw and the tip are used for guiding through a guide wire (not shown). In this case the guide wire, which is guided through the bone screw, is introduced through the skin of the patient and advanced through the tissue until it reaches the position where the bone screw is to be placed. The guide wire is inserted into the bone to the appropriate direction and depth. The bone screw is then guided along the guide wire extending therethrough until it reaches the surface of the bone and then screwed into the bone guided by the guide wire. This is in particular used in minimally invasive surgery ("MIS").

A second embodiment is now described with reference to FIGS. 9 to 13. Identical parts are designated with the same reference numerals and the description thereof is not repeated. The tubular body 1' of the second embodiment differs from the tubular body 1 of the first embodiment in that a recess in the form of a circumferential groove 60 is provided at the interior wall surface of the tubular body 1' at a distance from the first end 2 and from the internal thread 6. The groove 60 serves for engagement with a projection provided at a head 80.

Figure 9:
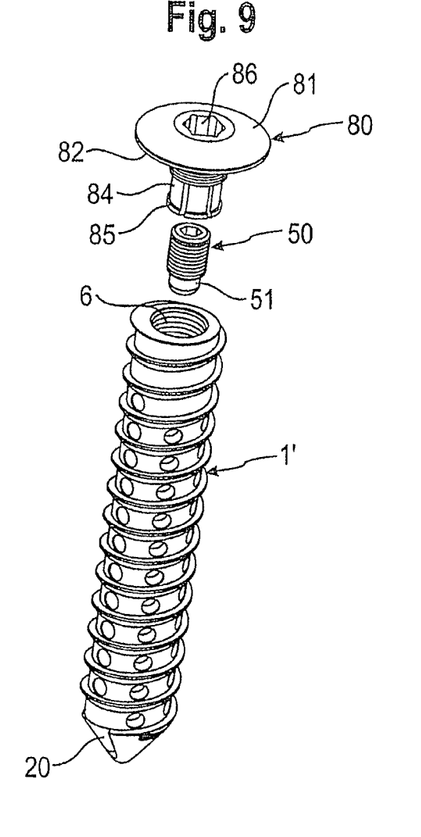
FIG. 9 shows a perspective exploded view of a bone screw according to a second embodiment.
Figure 10:
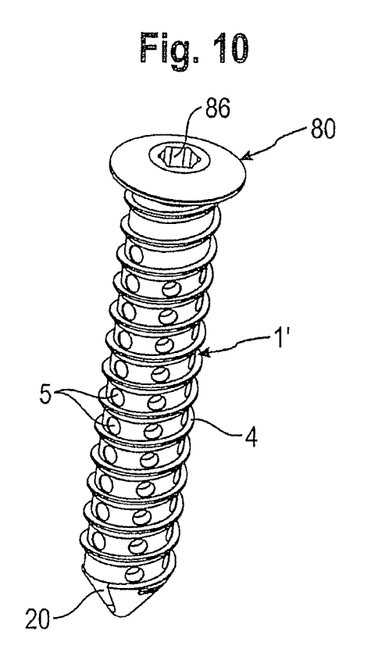
FIG. 10 shows a perspective view of the bone screw of FIG. 9 in an assembled state.
Figure 11:
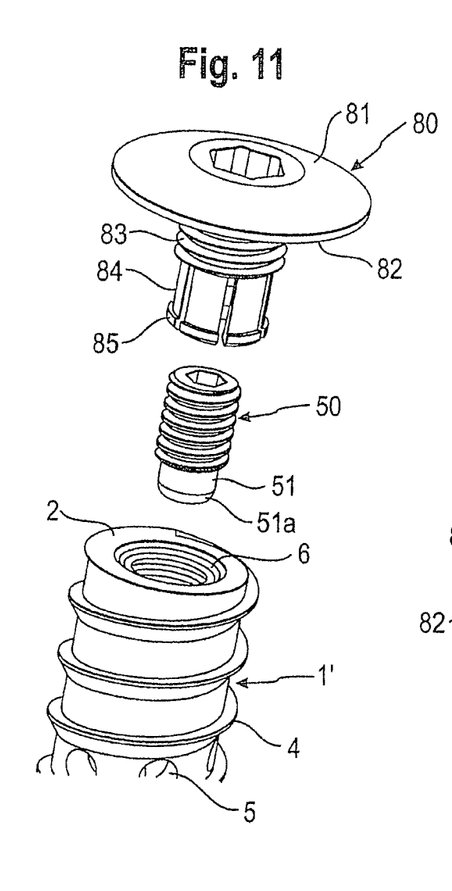
FIG. 11 shows an enlarged portion of the bone screw of FIG. 9 in an exploded view.
Figure 12:
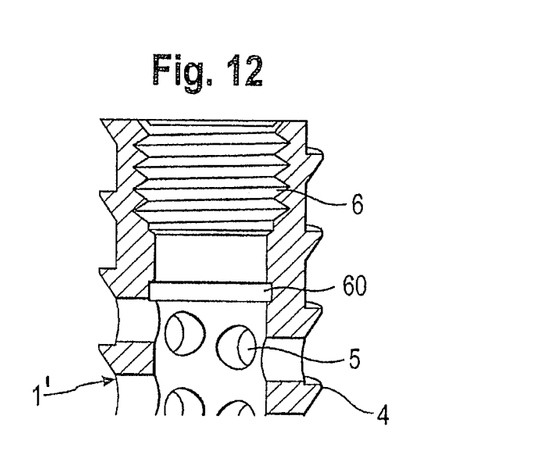
FIG. 12 shows an enlarged sectional view of a portion of the tubular portion of the bone screw of FIG. 9.

The head 80 has a first end 81 facing away from the tubular body 1' and a second end 82 facing the tubular body 1'. The surface of the first end 81 can be, for example, lens-shaped. The second end 82 comprises a flat surface providing an abutment for the bone surface. At its second end 82, the head 80 has a cylindrical projection having a first portion 83 with an external thread that cooperates with the internal thread 6 provided at the interior wall surface of the tubular body 1' adjacent the first end 2. Following the threaded portion 83 a substantially cylindrical portion with flexible wall sections 84 is provided. At the free end of each wall section 84, a projection 85 is provided, the shape of which is such that the projection 85 fits into the groove 60 of the tubular body 1'.

Figure 13:
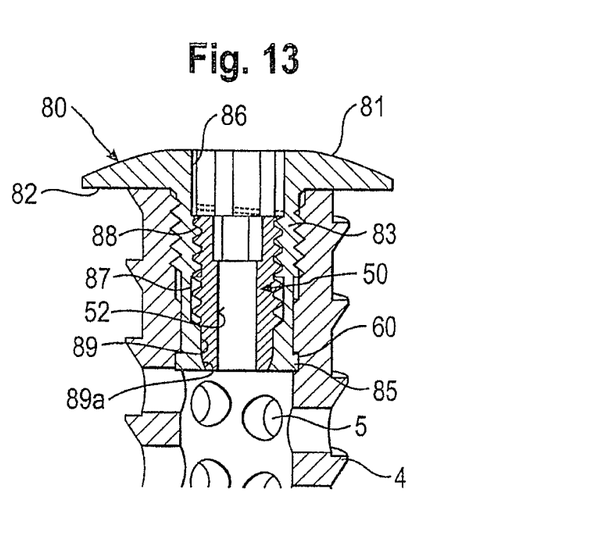
FIG. 13 shows an enlarged sectional view of the connection of the tubular body with the head of the bone screw of FIG. 11.

The axial length of the threaded projection 83 and the flexible wall sections 84 is such that, as shown in FIG. 13, when the head 80 is inserted into the tubular body 1' and the threaded connection between the portion 83 and the internal thread 6 is tightened, the projection 85 engages the groove 60.

Further, the head 80 has a recess 86 at its first end for engagement with a screw driver. The recess 86 is shown to be star-shaped but can have any polygon shape. A coaxial bore 87 extends through the head 80, which has a portion within an internal thread 88 adjacent the recess 86 and which has in the region of the flexible wall sections 84 a section 89 with a smaller inner diameter that tapers in a portion 89a towards the free end.

The securing element 50 according to the second embodiment is a set screw with a cylindrical projection 51 without a thread and with a taper 51a at its free end. The set screw can be screwed into the coaxial bore of the head 80 when the head 80 is inserted into the tubular body, and tightened until the tapered section 89a of the screw and the tapered section 51a of the head engage each other. By means of this, the flexible wall portions 84 are slightly pressed outwards, so that the projections 85 engage the groove 60. When the projections 85 engage the groove 60, the head 80 is secured to the tubular body 1' and cannot be loosened or disconnected. A coaxial bore 52 can be provided for guiding a guide wire therethrough.

Use of the bone screw according to the second embodiment is similar to the use of the bone screw according to the first embodiment. The description thereof will not be repeated.

Figure 14:
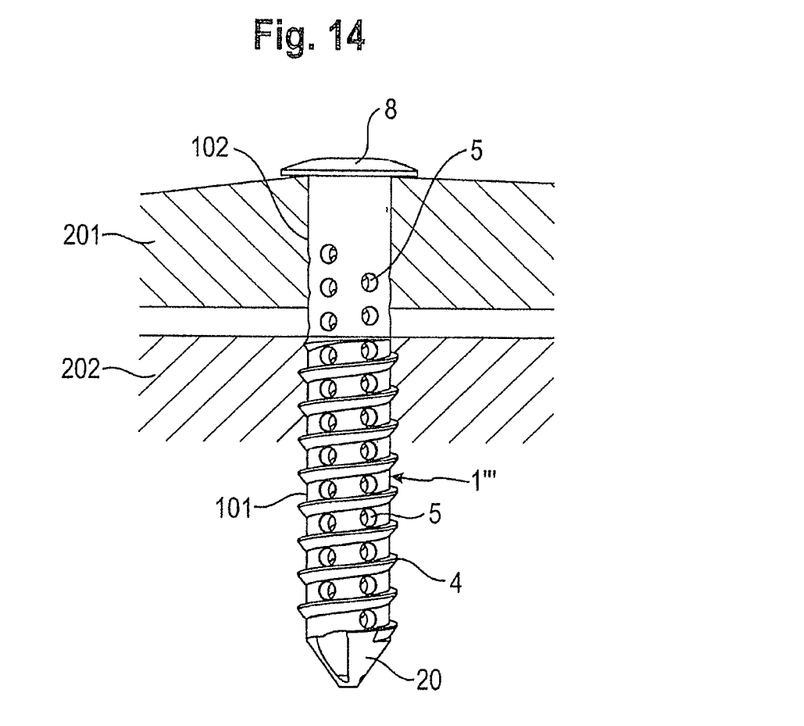
FIG. 14 shows a modified example of the bone screw according to the previous embodiments in a side view.

FIG. 14 shows a bone screw according to a modified embodiment of the previous embodiments. Head 8 and tip 20 can be that of the first embodiment, the second embodiment or the third embodiment. The tubular body 1''' has a first section 101 adjacent to the tip 20 comprising a bone thread 4, and a second section 102 adjacent to the head 8 with a smooth surface without a bone thread. The screw according to the modified embodiment can be used as a compression screw to press together two bone parts 201, 202. The bone screw is screwed into one bone part 202. In the other bone part 201 there is only a core hole, through which the first section 102 of the bone screw extends. By tightening the bone screw, the second end 10 of the head 8 abuts against the surface of the bone part 201 and presses the bone part 201 against the bone part 202. After a certain time, fusion of the bone parts 201, 202 with the bone screw and with each other takes place.

In a further modification, the second end 3 of the tubular body of all of the previous embodiments is free and the tip is omitted. In this case, the second end 3 can be provided with a plurality of cutting teeth that are configured to cut into the bone so that the cavity of the tubular body is automatically self-filled with cut bone material by screwing-in the bone screw into the bone.

In a further modification the outer diameter of the head may be equal to or even smaller than the outer diameter of the tubular body. This allows the bone screw to immerse fully into the bone.

In a further modification, the head and the tip are not cannulated.

What is claimed is:

1. A bone screw comprising:
    a tubular body having a first end and a second end, and comprising a tubular wall and at least one recess or at least one projection, wherein an exterior bone thread extends on an exterior surface of the tubular wall, and wherein the tubular wall further defines an inner cavity and a plurality of openings extending through the tubular wall into the inner cavity;
    a head that is separable from and connectable to the first end of the tubular body, the head having a first end and an opposite second end and defining an inner bore, the head comprising:
        an engagement structure to engage with a driver to advance the bone screw in a bone when the head is secured to the tubular body and when a rotating force from the driver is applied to the engagement structure in a first direction; and
        a connection structure comprising at least one projection or at least one recess to connect with the at least one recess or the at least one projection of the tubular body to connect the head to the tubular body; and
    a securing element configured to secure the head to the tubular body, wherein the securing element is configured to pass fully into the inner bore of the head when the securing element is assembled to the head and the tubular body;
    wherein when the head is secured to the tubular body, the first end of the head is outside the first end of the tubular body and the second end of the head is inside or adjacent the first end of the tubular body;
    wherein a diameter of the inner bore at the second end of the head is smaller than an outer diameter of a portion at the first end of the tubular body that is in direct contact with the head; and
    wherein when the head is secured to the tubular body by the securing element, the connection structure engages the tubular body in such a way that the head is locked against disconnection from the tubular body when a rotating force from a driver is applied to the engagement structure in a second direction opposite to the first direction to unscrew the bone screw back out of the bone.

2. The bone screw of claim 1, wherein the at least one recess or the at least one projection of the tubular body is provided at a distance from the first end of the tubular body.

3. The bone screw of claim 1, wherein the securing element secures the head to the tubular body independently from the force acting onto the head by the driver.

4. The bone screw of claim 1, wherein the securing element is an inner screw that is configured to be screwed into the inner bore of the head to secure the head to the tubular body.

5. The bone screw of claim 1, wherein a tip is provided at the second end of the tubular body.

6. The bone screw of claim 5, wherein the tip is a separate part from the tubular body.

7. The bone screw of claim 5, wherein the tip is formed integrally with the tubular body.

8. The bone screw according to claim 5, wherein the head and the tip are cannulated for guiding a guide wire.

9. The bone screw of claim 1, wherein the wall thickness of the tubular body is smaller than about 15% of an outer diameter of the tubular body.

10. The bone screw of claim 1, wherein the bone thread extends along the whole exterior surface of the tubular wall.

11. The bone screw of claim 1, wherein a portion of the exterior surface is without bone thread.

12. The bone screw of claim 11, wherein the portion of the exterior surface without bone thread is adjacent to the head.

13. The bone screw according to claim 1, wherein the head has a substantially flat portion providing an abutment against the tubular body.

14. The bone screw according to claim 1, wherein the head comprises a guiding hole configured to guide a wire therethrough.

15. The bone screw according to claim 1, wherein the tubular body is cylindrical.

16. The bone screw according to claim 1, wherein the engagement structure is a recess that is coaxial to a longitudinal axis of the bone screw and serves for engagement with the driver.

17. The bone screw according to claim 1, wherein the diameter of the inner bore is measured at a distalmost region of the inner bore.

18. A bone screw comprising:
a tubular body having a first end and a second end, and comprising a tubular wall defining an inner cavity having an internal thread, at least one recess different from the internal thread, and a plurality of openings extending through the tubular wall into the inner cavity, wherein an exterior bone thread extends on an exterior surface of the tubular wall;
a head that is separable from and connectable to the first end of the tubular body, the head comprising a projection having a first portion comprising an external thread for threading to the internal thread of the tubular wall and a second portion comprising a plurality of flexible wall sections and a projecting tab extending from each of the plurality of flexible wall sections configured to be received in the at least one recess of the tubular body;
a securing element configured to engage the head and urge the projecting tabs extending from the plurality of flexible wall sections into the at least one recess of the tubular body to secure the head to the tubular body; and
an engagement structure to engage with a driver to advance the bone screw in a bone when the head is connected to the tubular body and when a rotating force from the driver is applied to the engagement structure in a first direction;
wherein when the head is secured to the tubular body by the securing element, the projection engages the tubular body and the head is retained against relative rotation from the tubular body when a rotating force from a driver is applied to the engagement structure in a second direction opposite to the first direction to unscrew the bone screw back out of the bone.

19. The bone screw according to claim 18, wherein the head defines an inner bore with an internal thread, and wherein the securing element has an external thread, and wherein the securing element is insertable into the inner bore and threadable to the internal thread to urge the projecting tabs of the plurality of flexible wall sections of the head into the at least one recess of the tubular body.

20. A bone screw comprising:
a tubular body having a first end and a second end, and comprising a tubular wall and at least one recess or at least one projection, wherein an exterior bone thread extends on an exterior surface of the tubular wall, and wherein the tubular wall further defines an inner cavity and a plurality of openings extending through the tubular wall into the inner cavity;
a head that is separable from and connectable to the first end of the tubular body, the head having a first end and an opposite second end and defining an inner bore, the head comprising:
an engagement structure to engage with a driver to advance the bone screw in a bone when the head is secured to the tubular body and when a rotating force from the driver is applied to the engagement structure in a first direction; and
a connection structure comprising at least one projection or at least one recess to connect with the at least one recess or the at least one projection of the tubular body to connect the head to the tubular body; and
a securing element configured to secure the head to the tubular body, wherein the securing element is configured to pass fully into the inner bore of the head when the securing element is assembled to the head and the tubular body;
wherein when the head is secured to the tubular body, the first end of the head is outside the first end of the tubular body and the second end of the head is inside or adjacent the first end of the tubular body;
wherein a diameter of a distalmost region of the inner bore at the second end of the head is smaller than an outer diameter of a proximalmost region at the first end of the tubular body; and
wherein when the head is secured to the tubular body by the securing element, the connection structure engages the tubular body in such a way that the head is locked against disconnection from the tubular body when a rotating force from a driver is applied to the engagement structure in a second direction opposite to the first direction to unscrew the bone screw back out of the bone.

* * * * *